US008955179B2

(12) United States Patent
Yu

(10) Patent No.: US 8,955,179 B2
(45) Date of Patent: Feb. 17, 2015

(54) SURGICAL STATION

(71) Applicant: Chun Ho Yu, Hong Kong (HK)

(72) Inventor: Chun Ho Yu, Hong Kong (HK)

(*) Notice: Subject to any disclaimer, the term of this patent is extended or adjusted under 35 U.S.C. 154(b) by 0 days.

(21) Appl. No.: 13/959,782

(22) Filed: Aug. 6, 2013

(65) Prior Publication Data

US 2013/0318714 A1 Dec. 5, 2013

Related U.S. Application Data

(63) Continuation-in-part of application No. 12/721,512, filed on Mar. 10, 2010, now Pat. No. 8,528,136.

(30) Foreign Application Priority Data

Sep. 25, 2009 (HK) .................................. 09108883.4

(51) Int. Cl.
*A47B 7/00* (2006.01)
*A61B 19/00* (2006.01)
*A61G 13/10* (2006.01)

(52) U.S. Cl.
CPC ............... *A61B 19/28* (2013.01); *A61G 13/105* (2013.01)
USPC ..................................... 5/623; 5/503.1; 5/658

(58) Field of Classification Search
CPC .................. A61G 13/08; A61G 13/02; A61G 2013/0054; A61G 2007/0513; A61G 2013/0081; A61G 13/00; A61G 13/105; A47C 21/00; A47C 31/00
USPC .......... 5/612, 613, 513, 512, 621, 507.1, 624, 5/658, 503.1, 505.1, 623; 108/69, 73, 75, 108/143
See application file for complete search history.

(56) References Cited

U.S. PATENT DOCUMENTS

| 2,897,029 | A | * | 7/1959 | Maisel | 5/613 |
| 3,768,971 | A | * | 10/1973 | Fishpaw | 312/209 |
| 3,840,221 | A | * | 10/1974 | Hogan | 5/601 |
| 4,557,453 | A | * | 12/1985 | McCloskey | 248/287.1 |
| 5,152,486 | A | * | 10/1992 | Kabanek et al. | 248/201 |
| 5,362,021 | A | * | 11/1994 | Phillips | 248/276.1 |
| 5,681,018 | A | * | 10/1997 | Hoftman | 248/125.8 |
| 6,161,486 | A | * | 12/2000 | Boots | 108/48 |
| 6,266,831 | B1 | * | 7/2001 | Heimbrock | 5/601 |
| 6,493,890 | B2 | * | 12/2002 | Smeed | 5/503.1 |
| 7,523,514 | B2 | * | 4/2009 | Salt et al. | 5/503.1 |
| 7,628,439 | B1 | * | 12/2009 | Strong | 296/26.03 |
| 8,100,062 | B1 | * | 1/2012 | Anghel | 108/69 |
| 2003/0145381 | A1 | * | 8/2003 | Higdon et al. | 5/507.1 |
| 2007/0094798 | A1 | * | 5/2007 | Yu | 5/621 |
| 2007/0253764 | A1 | * | 11/2007 | Clayton et al. | 403/122 |
| 2010/0047012 | A1 | * | 2/2010 | Kull et al. | 403/325 |

* cited by examiner

*Primary Examiner* — Michael Trettel
*Assistant Examiner* — Richard G Davis

(57) ABSTRACT

A surgical station (50), including a patient support base (300) and an operation platform (60), wherein the patient support base is adapted for mounting on a patient bed. The operation platform includes a first platform portion (100) and a second platform portion (200). The second platform portion is moveably connected to said first platform portion such that said first and second platform portions are moveable between a preparation configuration and an operation configuration. The first and second platform portions collectively form a support platform surface (115/215) for supporting the hands of an operator in the operation configuration, such that the operator can operate catheters, guide wires or other surgical instruments with stable hands during surgical operation, wherein said first platform portion is mounted on said patient support base.

18 Claims, 5 Drawing Sheets

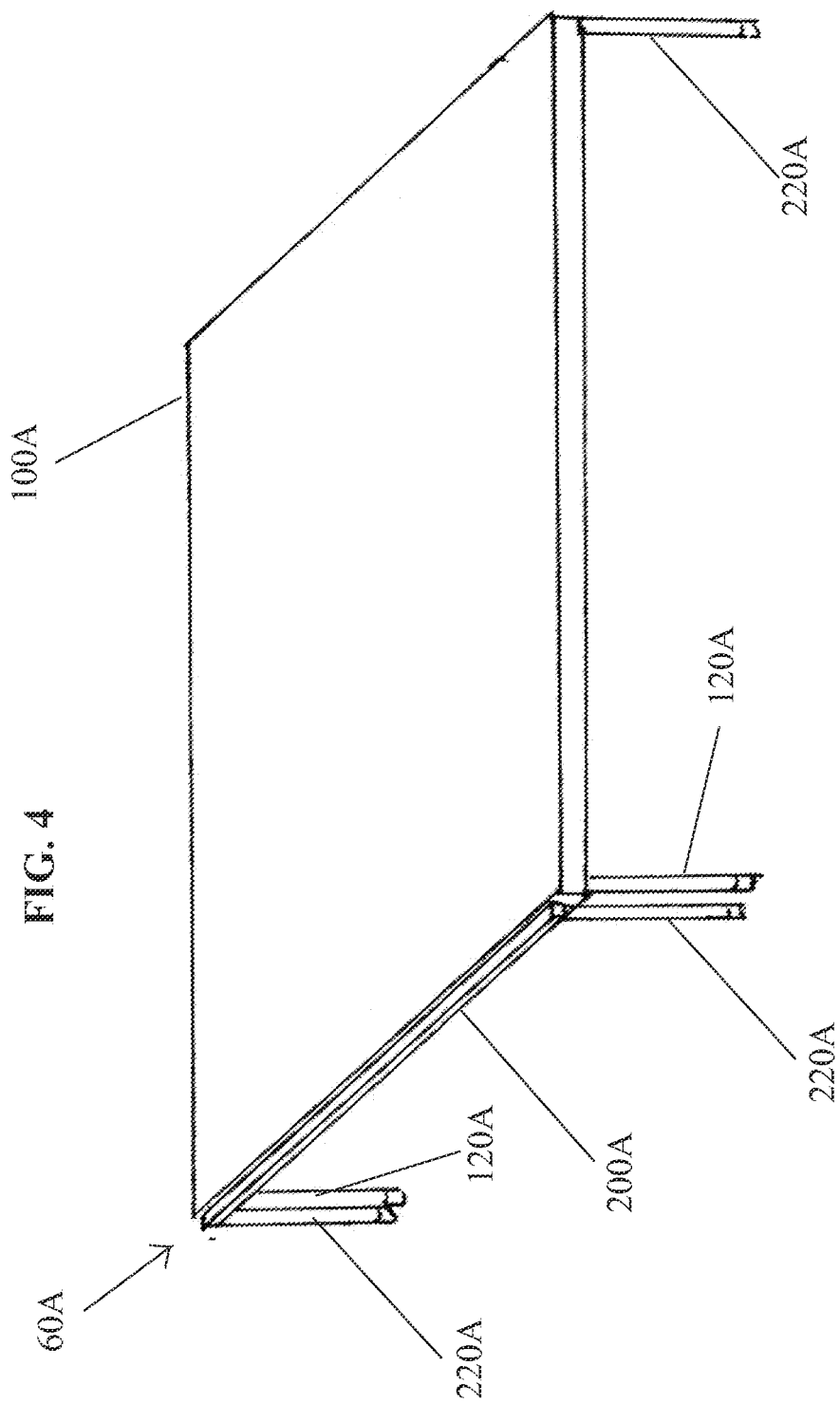

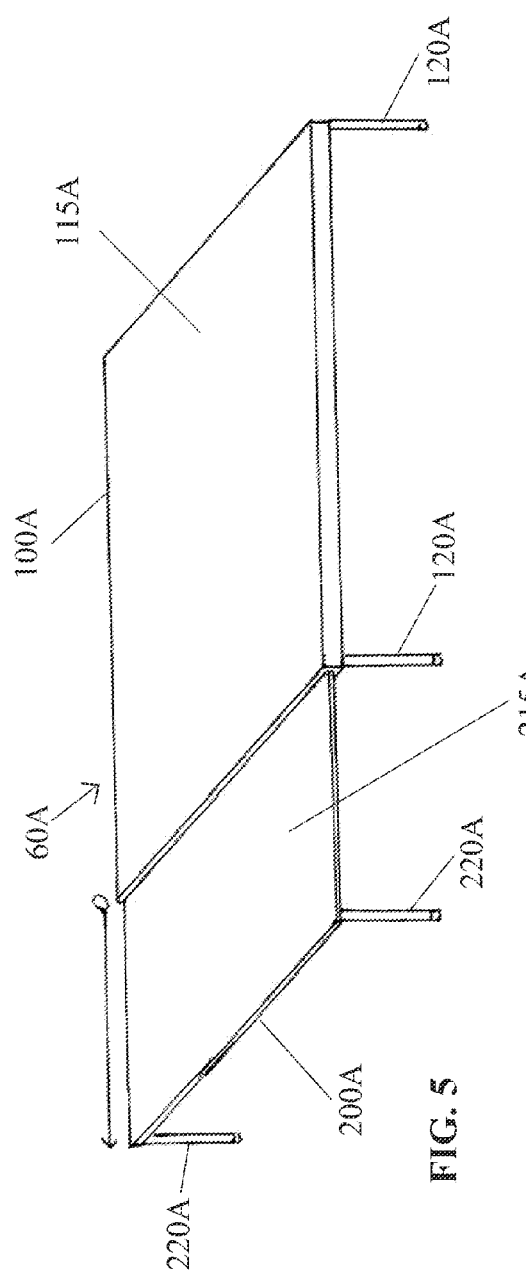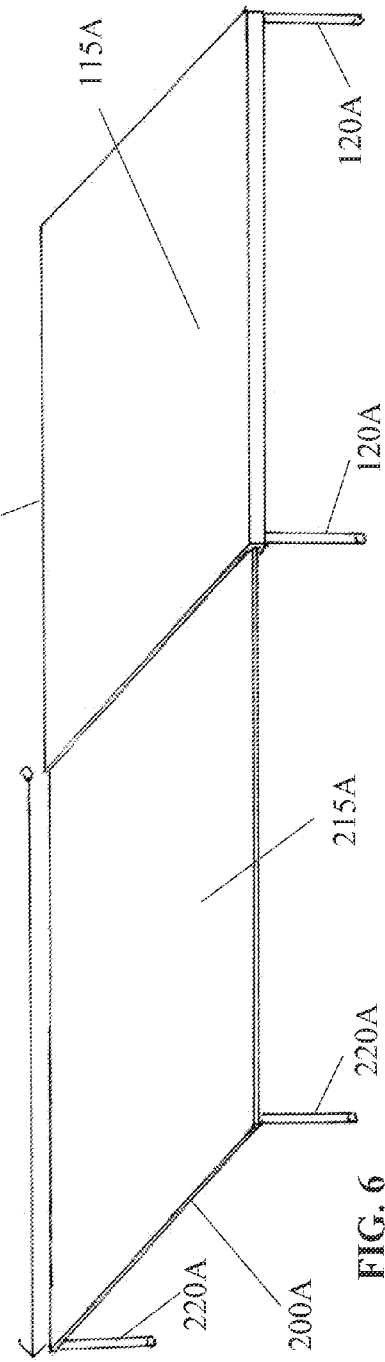

SURGICAL STATION

CROSS-REFERENCE TO RELATED APPLICATIONS

This application is a Continuation-In-Part in accordance to MPEP 201.08 to Utility Application 12/721,512 filed on Mar. 10, 2010 which claimed the Foreign Priority of HK Application 09108883.4 filed on Sep. 25, 2009.

FIELD OF THE INVENTION

The present invention relates generally to an accessory of an operating bed which facilitates image guided diagnostic and therapeutic medical operative procedures.

BACKGROUND OF THE INVENTION

Description of the Prior Art

The present invention may be used in image guided diagnostic and therapeutic medical operative procedures, which are often performed in a delicate manner with specialized instruments such as a catheter and guide wire. Examples of such procedures are vascular and interventional radiological procedures for endovascular treatment of cancers and cerebrovascular diseases, and angioplasty and stenting procedures for diseased vessels such as heart vessels. During such procedures, the operator, who may be a physician, surgeon, or other individual, inserts instruments such as the catheter and guide wire into the patient's body to reach the target organ. The operator may remotely control the instruments outside the patient's body to operate on the target organ. The operator often monitors the operation through a monitor displaying the situation of the surgical area inside the patient's body.

The performance of the operation requires accurate tracking and precise positioning of the catheter and guide wire at the target location through line manipulation of the instruments outside the patient's body. Such manipulation is currently performed by the operator with hands holding the instruments and resting on the patient's body.

Currently, the operator holds the catheter while resting their hand on the patient's body during fixation of the instruments, and simultaneously using their other hand to advance, withdraw, and/or rotate the catheter, and/or guide wire, or other instruments. Such manipulation requires a high degree of skill and dexterity to hold and control the catheter and guide wire steadily at the same time.

In current practice the operator's hands tire quickly, which makes it more difficult for the operator to control the instruments precisely. Though the hands of the operator may rest on the patient's body, the body surface is irregular and curved and the body moves from time to time due to pain suffered by the patient during the operation. As precise manipulation of the catheter and guide wire is of utmost importance, especially when the operation is conducted on blood vessels in the brain, for example, operators are looking for a stable working surface which can support their arms and hands.

Moreover, instruments with sharp points and edges which are placed on the patient's body may accidentally injure the patient. The patient's body may also be exposed to fluids used for continuous irrigation of the instruments during the operation. Operators are looking for a device which overcomes the foregoing shortcomings and which provides, for example, a large shield to cover and protect the patient's body.

Catheters and guide wires are typically long and occupy considerable space. In current practice, the catheters and guide wires are placed on the patient's body for easy access and convenient handling. The body is irregular and curved. The catheter and guide wire arc significantly longer than the operating bed. As such, the catheters, guide wires, and other instruments cannot always be arranged in an orderly manner on the patient's body.

During the operation, an assistant is typically required lo hold the catheter and guide wire at the end of the operating bed to avoid the catheter and guide wire from slipping off the patient's body and the operation table. If the catheter and guide wire slips off, it may pull the catheter and guide wire out of the operating area of the patient's body and thus cause serious injury to the patient. Existing platforms, such as that disclosed in international publication WO 99/23965, cannot provide a flat and large working surface for placing the instruments and apparatus in an orderly manner and prevent the catheter and guide wire from slipping off. Accordingly, there is a further need for a system that will also free the assistant from holding the catheter and guide wire so that they can be assigned to perform other duties.

There is therefore a need for a surgical station to be placed on the operating or patient bed which provides a large working surface for the operator to perform image guided diagnostic and therapeutic medical operative procedure. Such surgical station should be easily attachable to the operating or patient bed and allows convenient access of the patient lo lie thereon.

SUMMARY OF THE PRESENT INVENTION

An object of the present invention is to provide an add-on working surface to an operating bed for an operator to perform image guided diagnostic and therapeutic medical operative procedure.

An embodiment of the present invention provides a surgical station, including a patient support base and an operation platform, wherein the patient support base is adapted for mounting on a patient bed. The operation platform includes a first platform portion and a second platform portion. The second platform portion is moveably connected to said first platform portion such that said first and second platform portions are moveable between a preparation configuration and an operation configuration. The first and second platform portions collectively form a support platform surface for supporting the hands of an operator in the operation configuration, such that the operator can operate catheters, guide wires or other surgical instruments with stable hands during surgical operation, wherein said first platform portion is mounted on said patient support base.

In another embodiment of the present invention, the first and second platform portions are foldable into the preparation configuration and un-foldable into the operation configuration.

In another embodiment of the present invention, the first and second platform portions are connected by a hinge, such that the second platform portion is moveable relative to the first platform portion between the preparation and operation configurations about the hinge.

In yet another embodiment of the present invention, the second platform section is extendable from the first platform section and is slidably connected.

In yet another embodiment of the present invention, the second platform portion further comprising supporting member adjustable in height.

Further, in another embodiment of the present invention, the first platform portion is releasably attached to said patient support base.

The advantage of the present invention is that a surgical station is readily to be placed on the operating or patient bed which provides a large working surface for the operator to perform image guided diagnostic and therapeutic medical operative procedure. The surgical station is easily attachable lo the operating or patient bed and allows convenient access of the patient to lie thereon.

BRIEF DESCRIPTION OF THE DRAWINGS

The above and other aspects, features, and advantages of the present invention will become more apparent upon consideration of the following description of preferred embodiments, taken in conjunction with the accompanying drawing figures, wherein:

FIG. 4 is a perspective view of another embodiment of an extendable surgical station in the preparation configuration.

FIG. 5 is a perspective view of the extendable surgical station in the operation configuration.

FIG. 6 is a perspective view of the extendable surgical station in the operation configuration.

DETAILED DESCRIPTION OF THE PREFERRED EMBODIMENTS

In the following detailed description, reference is made to the accompanying drawing figures which form a part hereof, and which show by way of illustration specific embodiments of the invention. It is to be understood by those of ordinary skill in this technological field that other embodiments may be utilized, and structural, as well as procedural changes may be made without departing from the scope of the present invention.

Figure 1:
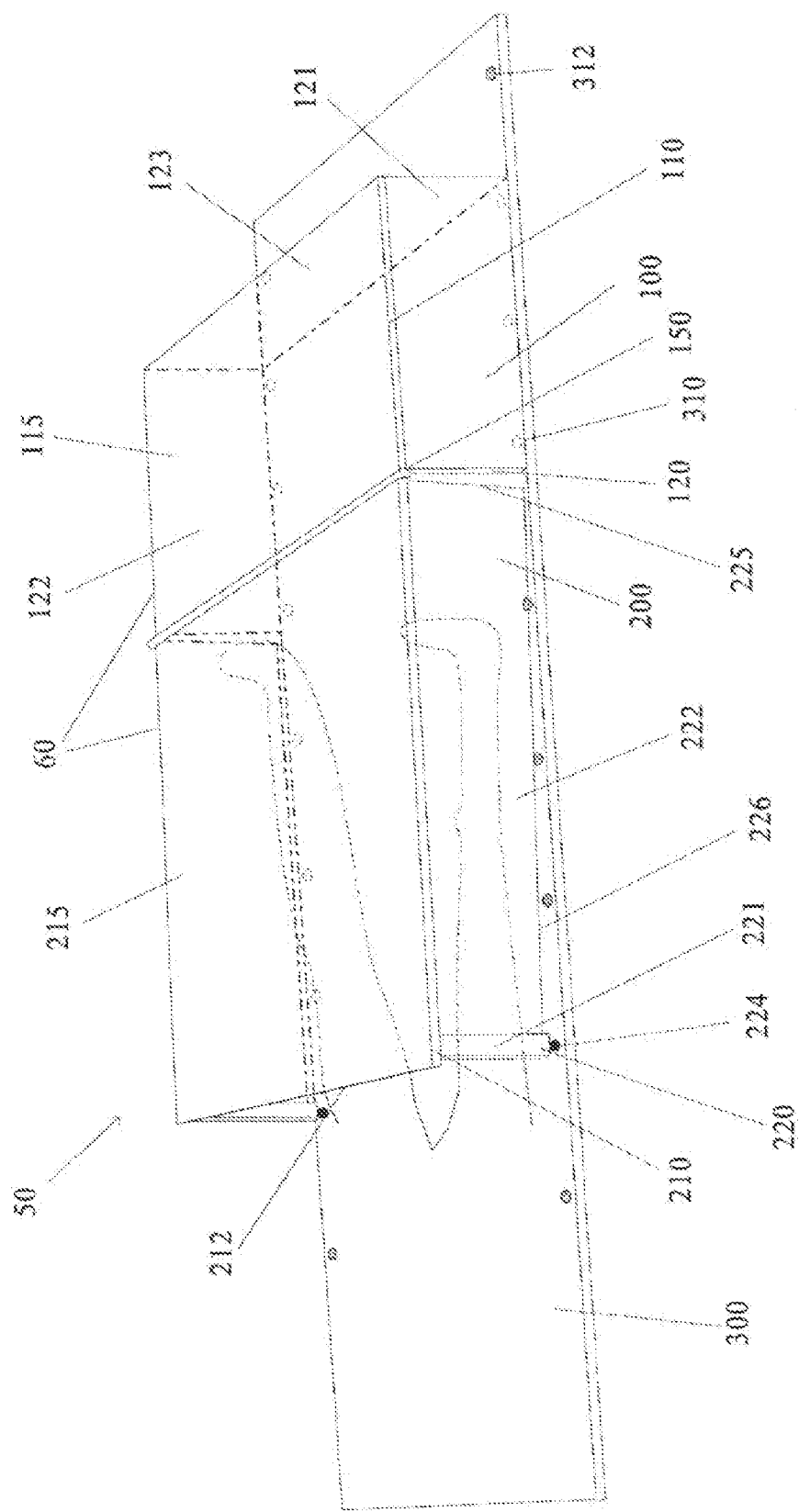
FIG. 1 is a perspective view of an embodiment of the surgical station in a operation Configuration.

As illustrated in FIG. 1, an embodiment of a surgical station 50 of the present invention includes an operation platform 60 and a patient support base 300 for supporting the 20 operation platform. The patient support base 300 is slightly shorter than the length of an ordinary operating bed (in the following description, the reference to an operating bed also applies to a patient bed) with a width as an ordinary operating bed, and is to be attached to the top surface of the operating bed (not shown), for example by magnet attached under the patient support base 300.

The operation platform 60 includes a first platform portion 100 and a second platform portion 200. During the operation, the patient will lie on the patient support base. The first and second platform portions 100/200 are adapted for receiving part of the patient's body. The first and second platform portions 100/200 includes a first top portion 110 and a second top portion 210 respectively for covering part of a patient's body (in FIG. 1, the lower body part), so that a flat platform support surface 115/215 is provided for supporting lengthy instruments and apparatus, such as catheters and guide wires and for the operator to 10 manipulate the instruments thereon. For clarity, further description of the present invention will be provided with reference to the term "instruments," but such teachings apply equally to others devices and apparatus involved in the operation procedure.

The patient support base 300 will be placed over the operating bed, effectively covering and extending over a lengthwise portion of the top surface of the operating bed. 15 The first and second platform portions 100/200 may be releasably attached to the patient support base 300, and may be arranged so that it is proximate to the situs of the surgical procedure on the patient (for example, legs, torso, or head). This is typically accomplished by arranging the first and second platform portions 100/200 at or near the center of the operating bed. Such arrangement allows the operator to arrange the instruments on the 20 platform support surface 115/215 in an orderly manner, and permits manipulating of the instruments during the operation.

Figure 2:
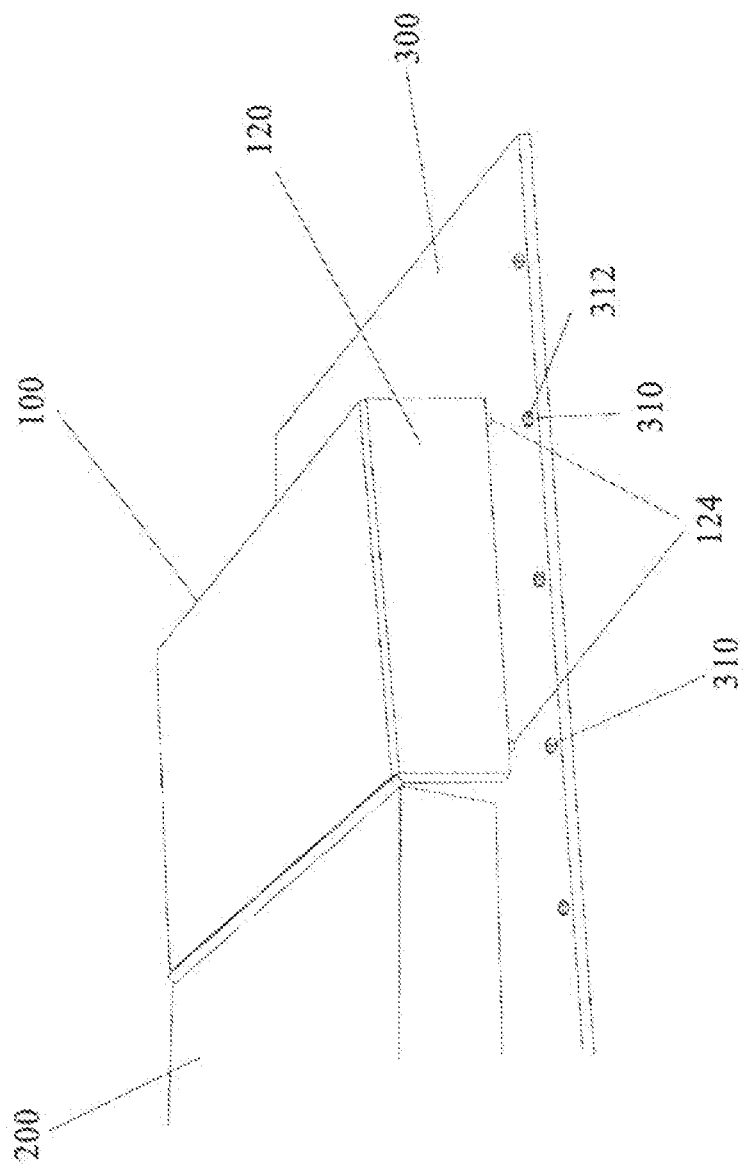
FIG. 2 is a partial view of the surgical station of FIG. 1 showing an embodiment of the supporting member.

As shown in FIG. 2, the first platform portion 100 includes a first supporting member 120 which may be releasably attached to the patient support base 300. The first supporting member 120 may be side walls 121/122 with metal legs 124 extending from the bottom of the side walls which are inserted into holes 310 having magnetic base 312 disposed on the sides of the patient support base 300. The rear wall 123 may or may not be present, as it is sufficient to have two side walls 121/122 for support. In another embodiment, the first supporting member 120 may not contain a side wall, but may merely contain four legs extending from the four corners of the bottom of the first top portion 110 to the holes 310. The position of the first platform portion 100 may therefore be adjusted along the length of the operating bed.

Figure 3:
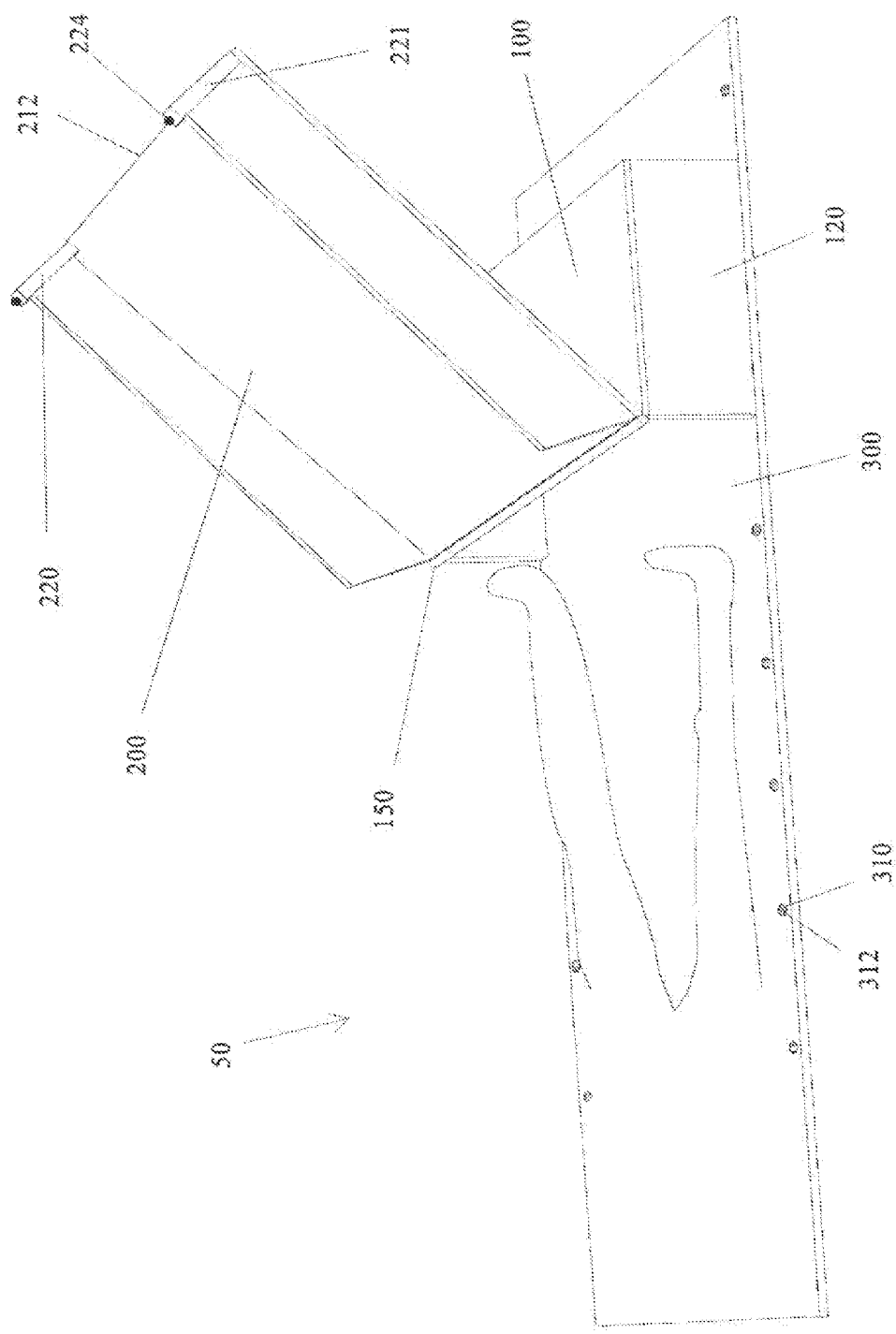
FIG. 3 is a perspective view of the surgical station of FIG. 1 in a preparation configuration.

The second top portion 210 of the second platform portion 200 may be attached with the first top portion 110 by a hinge joint 150 such that the top-up portion 50 can operate between a preparation configuration and an operation configuration. As shown in FIG. 3, in the preparation configuration, the second platform portion 200 may be folded and flipped over the first platform portion 100, to allow easy access of the patient's body into the first platform portion 100. In the operation configuration, the second platform portion 200 is flipped down to cover the patient's body. The second top portion 210 may further extend out at an open end 212 lo form a larger working surface 215. When unfolded in the operation configuration, the first and second top portions 110/210 form a Hat platform support surface 115/215 for the operator to lie out and manipulate the instruments, in particular the long catheters and guide wires.

The second platform portion 200 includes a second supporting member 220 extending from the bottom of the second top portion 210 and releasably attached to the patient support base 300. The second supporting member 220 may be side walls with metal legs extending from the bottom of the side walls which are inserted into holes 310 having magnetic base 312 disposed on the sides of the patient support base 300. In the embodiment as shown in FIG. 1, the second supporting member 220 is a telescopic leg member 221 adjustable in height. The open end 212 of the second top portion 210 may be lowered toward the patient's body to form a slope which prevents an abrupt drop of catheters and guide wires 5 from the platform support surface 215 on to the patient.

The lower end of the leg member 221 has a ball-shaped base 224 made of metal to allow a stable contact with the magnetic base 312 at various angles of the second top portion 210 and heights of the leg member 221. In the embodiment as shown in FIG. 3, the side wall 222 has cut-out portions 225/226 adjacent to the side wall 121 and the patient support base 300 to allow the second top portion 210 to lower at a certain angle. The side wall 222 may or may not be present, as it is sufficient to have two leg members 221 for support. The line of holes 310 allows the first and second platform portions 100/200 to be positioned at different locations along the length of the operating bed. The holes 310 at the patient support base 300 for positioning the patient's upper body may not contain the magnet base which 15 may become a radioopague obstacle in the operation procedure.

Some or all of the above-described components, including first and second top portions 110/210, first and second supporting members 120/220, side walls 121/122/123/222 and leg member 221 may be formed from X-ray transmittable materials so that these components are compatible with X-ray equipment. Additionally or alternatively, such 20 components may be formed from a transparent material, such as Perspex Acrylic, plastic, or silicon, to enable the operator to view the patient during the operation.

In another embodiment of the operation platform 60A as seen in FIG. 4-6, the second platform portion is extendable from the first platform portion and is slidably connected.

As seen in FIG. 4, the preparation configuration may be achieved when the second platform portion 200A is retracted within the first platform portion 100A. This retractable embodiment of the operation platform also allows for effortless storage when not in use.

FIG. 5-6 shows the second platform portion 200A extended from the first platform portion 100A in multiple positions, thus increase the total surface area 115A and 215A of the operation platform 60A depending on the length of total extension. The second platform portion 200A is slidably connected to the first platform section 100A to allow the second platform portion 200A to be extended and adjusted in multiple lengths to accommodate the need of the operators or the size of the patient. Ball bearing sliding brackets may be used to slidably connect the first and second platform portions to allow smooth extension and sliding of the second platform portion 200A from the first platform section 100A. Other alternatives such as grooving, sliding rails and other means to facilitate the extendibility of the second platform section 200A from the first platform section 100A may also be used.

In this embodiment, the first platform section 100A is supported by supporting members 120A which are ideally positioned to accommodate the line of holes 310 on the patient support base 300. The supporting members 120A may be adjustable in height and location, and may be detachable and/or foldable. The supporting members 120A may also contain tipping that can releasably and selectively engage with the holes or mounts of the patient support base 300. The second platform section 200A is also supported by supporting members 220A which may be adjustable in height and location and may be detachable and/or foldable. The supporting members 220A may also contain tipping that can releasable and selectively engage with the holes or mounts of the patient support base 300.

Like other embodiments, the position of the first and second platforms 100A/200A can be adjusted along the length of the operating bed. The line of holes 310 allows the first and second platform portions 100A/200A to be positioned at different locations along the length of the operating bed. More specifically, the second platform portion can slidably extend out to multiple lengths to accommodate the positions of the holes 310 based on the needs of the operators and/or patients.

While the invention has been described in detail with reference to disclosed embodiments, various modifications within the scope of the invention will be apparent to those of ordinary skill in this technological field. It is to be appreciated that features described with respect to one embodiment typically may be applied to other embodiments.

What is claimed is:

1. A surgical station comprising a patient support base and an operation platform:

wherein the patient support base is adapted for mounting on a surface of a patient bed and is shorter than length of an ordinary patient bed, the operation platform comprises a first platform portion and a second platform portion, the second platform portion is slidably connected to said first platform portion such that said first and second platform portions are moveable between a preparation configuration and an operation configuration, said first and second platform portions collectively forming a support platform surface for supporting the hands of an operator in the operation configuration, such that the operator can operate catheters, guide wires or other surgical instruments with stable hands during surgical operation, the first and second platform portions comprise a plurality of supporting members wherein the supporting members of the first platform portion and the second platform portion are adapted to releasably and selectively engage with patient support base to allow adjustment of position of the operation platform, wherein the said patient support base is provided with two lines of holes disposed along the lengthwise direction of the patient support base, each line of holes is located proximate to the respective longitudinal edge of the patient support base and the said supporting members of the first platform portion and the second platform portion are adapted to releasably and selectively engage with the said holes on the patient support base to allow adjustment of position of the operation platform.

2. The surgical station according to claim 1, wherein the first and second platform portions are extendable into the preparation configuration and retractable into the operation configuration.

3. The surgical station according to claim 1, wherein the first and second platform portions are connected by ball bearing sliding brackets such that the second platform portion is moveable relative to the first platform portion between the preparation and operation configurations.

4. The surgical station according to claim 1, wherein the second platform portion further comprising supporting member adjustable in height.

5. The surgical station according to claim 1, wherein the first platform portion is releasably attached to said patient support base.

6. The surgical station according to claim 1, wherein the first platform portion further comprising a flat top surface.

7. The surgical station according to claim 1, wherein the second platform portion further comprising a flat top surface.

8. The surgical station according to claim 1, wherein the first platform portion is adapted for receiving part of a patient's body.

9. The surgical station according to claim 1, wherein the second platform portion is adapted for receiving part of a patient's body.

10. A surgical station comprising a patient support base and an operation platform:

wherein the patient support base is adapted for mounting on a surface of a patient bed and is shorter than length of an ordinary patient bed, the operation platform comprises a first platform portion and a second platform portion, the second platform portion is slidably connected to said first platform portion such that said first and second platform portions are moveable between a preparation configuration and an operation configuration, said first and second platform portions collectively forming a support platform surface for supporting the hands of an operator in the operation configuration, such that the operator can operate catheters, guide wires or other surgical instruments with stable hands during surgical operation, wherein the patient support base is provided with two lines of holes disposed along the lengthwise direction of the patient support base, each line of holes is located proximate to the respective longitudinal edge of the patient support base, the first and second platform portions comprise a plurality of supporting members, wherein the supporting members of the first platform portion and the second platform portion are adapted to releasably and selectively engage with the holes and mount on the patient support base to allow adjustment of position of the operation platform, wherein the supporting member is a leg member and a lower end of the leg member has a ball-shaped base made of metal.

11. The surgical station according to claim 10, wherein the first and second platform portions are extendable into the preparation configuration and retractable into the operation configuration.

12. The surgical station according to claim 10, wherein the first and second platform portions are connected by ball bearing sliding brackets such that the second platform portion is moveable relative to the first platform portion between the preparation and operation configurations.

13. The surgical station according to claim 10, wherein the second platform portion further comprising supporting member adjustable in height.

14. The surgical station according to claim 10, wherein the first platform portion is releasably attached to said patient support base.

15. The surgical station according to claim 10, wherein the first platform portion further comprising a flat top surface.

16. The surgical station according to claim 10, wherein the second platform portion further comprising a flat top surface.

17. The surgical station according to claim 11, wherein the first platform portion is adapted for receiving part of a patient's body.

18. The surgical station according to claim 10, wherein the second platform portion is adapted for receiving part of a patient's body.

* * * * *